US011525008B2

(12) United States Patent
Raby et al.

(10) Patent No.: US 11,525,008 B2
(45) Date of Patent: Dec. 13, 2022

(54) METHODS AND PHARMACEUTICAL COMPOSITIONS FOR THE TREATMENT OF LUNG CANCER (71) Applicants: INSERM (INSTITUT NATIONAL DE LA SANTÉ ET DE LA RECHERCHE MÉDICALE), Paris (FR); UNIVERSITÉ DE REIMS CHAMPAGNE-ARDENNE, Reims (FR); CENTRE HOSPITALIER UNIVERSITAIRE DE REIMS, Reims (FR)

(72) Inventors: Béatrice Raby, Reims (FR); Amina Jouida, Reims (FR); Myriam Polette, Reims (FR)

(73) Assignees: INSERM (INSTITUT NATIONAL DE LA SANTÉ ET DE LA RECHERCHE MÉDICALE), Paris (FR); UNIVERSITÉ DE REIMS CHAMPAGNE-ARDENNE, Reims (FR); CENTRE HOSPITALIER UNIVERSITAIRE DE REIMS, Reims (FR)

( * ) Notice: Subject to any disclaimer, the term of this patent is extended or adjusted under 35 U.S.C. 154(b) by 545 days.

(21) Appl. No.: 16/335,880

(22) PCT Filed: Sep. 21, 2017

(86) PCT No.: PCT/EP2017/073874
§ 371 (c)(1),
(2) Date: Mar. 22, 2019

(87) PCT Pub. No.: WO2018/055023
PCT Pub. Date: Mar. 29, 2018

(65) Prior Publication Data
US 2019/0256611 A1    Aug. 22, 2019

(30) Foreign Application Priority Data

Sep. 22, 2016 (EP) ................................ 16306213

(51) Int. Cl.
| *C07K 16/30* | (2006.01) |
| *A61P 35/00* | (2006.01) |
| *A61K 31/05* | (2006.01) |
| *A61K 31/137* | (2006.01) |
| *A61K 31/255* | (2006.01) |
| *A61K 31/4706* | (2006.01) |
| *A61K 31/506* | (2006.01) |
| *A61K 31/517* | (2006.01) |
| *A61K 31/519* | (2006.01) |
| *A61K 31/5355* | (2006.01) |
| *C12Q 1/6886* | (2018.01) |

(52) U.S. Cl.
CPC .............. *C07K 16/30* (2013.01); *A61K 31/05* (2013.01); *A61K 31/137* (2013.01); *A61K 31/255* (2013.01); *A61K 31/4706* (2013.01); *A61K 31/506* (2013.01); *A61K 31/517* (2013.01); *A61K 31/519* (2013.01); *A61K 31/5355* (2013.01); *A61P 35/00* (2018.01); *C12Q 1/6886* (2013.01); *C12Q 2531/113* (2013.01); *C12Q 2561/113* (2013.01); *C12Q 2565/101* (2013.01); *C12Q 2600/106* (2013.01); *C12Q 2600/158* (2013.01)

(58) Field of Classification Search
CPC ................ A61P 35/00; G01N 2800/52; G01N 33/57484; G01N 33/57423; C07K 16/30; C12Q 1/6886; C12Q 2600/158; C12Q 2600/106; C12Q 2600/112; C12Q 2600/118
See application file for complete search history.

(56) References Cited

FOREIGN PATENT DOCUMENTS

| WO | WO-0222636 A1 * | 3/2002 | .......... C12N 15/1138 |
| WO | WO-2010006027 A1 * | 1/2010 | ........... C12Q 1/6841 |

OTHER PUBLICATIONS

Toledo, G., Sola, J. J., Lozano, M. D., Soria, E., & Pardo, J. (2004). Loss of FHIT protein expression is related to high proliferation, low apoptosis and worse prognosis in non-small-cell lung cancer. Modern pathology 17(4), 440-448 (Year: 2004).*
Ji et al. (Ji, L., Fang, B., Yen, N., et al. Induction of Apoptosis and Inhibition of Tumorigenicity and Tumor Growth by Adenovirus Vector-mediated Fragile Histidine Triad (FHIT) Gene Overexpression. (1999) Cancer Research 59: 3333-3339) (Year: 1999).*
Swisher et al. ((2015) Induction of p53-regulate Genes and tumor Regression in Lung Cancer Patients after Intratumoral Delivery of Adenoviral p53 (INGN 201) and Radiation Therapy. Clinical Cancer Research, 9: 2193-2198) (Year: 2015).*
Abstract of Jiang et al (Zhonghua Zhongliu Fangzhi Zazhi (2007), 14(24), 1875-1878 (Year: 2007).*
Slastnikova et al (2018 Frontiers in Pharmacology, vol. 9, pp. 1-21) (Year: 2018).*
Lorenzer et al (Journal of Controlled Release, 2015, vol. 203, pp. 1-15) (Year: 2015).*

(Continued)

Primary Examiner — Karen A. Canella
(74) Attorney, Agent, or Firm — WCF IP (57) ABSTRACT The present invention relates to methods and pharmaceutical compositions for the treatment of lung cancer. The inventors showed that FHIT (also known as bis(5-adenosyl)-triphosphatase) regulates HER2 activity in lung tumor cells and that HER2 inhibitors reduce invasion induced by FHIT inhibition. In particular, the present invention relates to a method of treating lung cancer in a patient in need thereof comprising the steps of i) determining the expression level of FHIT in a tumor tissue sample obtained from the patient, ii) comparing the expression level determined at step i) with a predetermined reference value and iii) administering to the patient a therapeutically effective amount of at least one HER2 inhibitor when the expression level determined at step i) is lower than the predetermined reference level.

6 Claims, 4 Drawing Sheets

(56) References Cited

OTHER PUBLICATIONS

Merkel et al (Advanced Drug Delivery Reviews, 2014, vol. 75, pp. 112-128) (Year: 2014).*
Rao et al (Advanced Drug Delivery Reviews, 2009, vol. 61, pp. 746-759) (Year: 2009).*
Moore et al ('Short Hairpin RNA (shRNA): Design, Delivery, and Assessment of Gene Knockdown', In: RNA Therapeutics, M. Sioud, Ed., Methods in Molecular Biology, 2010, vol. 629, pp. 139-156) (Year: 2010).*
Zhang et al (American Journal of Pathology, 2007, vol. 170, pp. 366-376) (Year: 2007).*
(Zambrano et al, Pharmacological Research, 2017, vol. 119, pp. 188-194 (Year: 2017).*
Wei Yan et al: "The clinicopathological significance of FHIT hypermethylation in non-small cell lung cancer, a meta-analysis and literature review", Scientific Reports, vol. 6, Jan. 22, 2016, p. 19303.
Francesca Bianchi et al: "Fhit Expression Protects Against HER2-Driven Breast tumor Development: Unraveling the Molecular Interconnections", Cell Cycle, vol. 6, No. 6, Mar. 15, 2007, pp. 643-646.
Hisayuki Shigematsu et al: "Somatic mutations of epidermal growth factor receptor signaling pathway in lung cancers", International Journal of Cancer, vol. 119, No. 2, Jan. 15, 2006, pp. 257-262.

* cited by examiner

METHODS AND PHARMACEUTICAL COMPOSITIONS FOR THE TREATMENT OF LUNG CANCER

FIELD OF THE INVENTION

The present invention relates to methods and pharmaceutical compositions for the treatment of lung cancer.

BACKGROUND OF THE INVENTION

Lung cancers consist of two major histological types, non-small-cell lung carcinoma (NSCLC) and small-cell lung carcinoma. NSCLC consists of squamous cell carcinoma (SCC), adenocarcinoma (AD), large-cell carcinoma, and others. NSCLC accounts for ~85% of all lung cancers, and there are ~80% of NSCLC cases in advanced stage where the prognosis remains poor. Therefore, investigation of the mechanism of initiation, progression, and identification of prognostic markers is still needed for the selection of patients with NSCLC and to provide better individualized treatment.

FHIT, also known as bis(5-adenosyl)-triphosphatase, is one of the histidine triad gene family members and is an enzyme encoded by the FHIT gene. The FHIT gene locates the most common fragile site in the human genome, FRA3B (3p14.2), a region which frequently undergoes genomic rearrangement, biallelic loss, and cytogenetic abnormalities in tumors. Previous reports showed that FHIT was inactivated by the loss of heterozygosity and methylation in cancer cells, which indicated that FHIT is a tumor suppressor protein. Its precise function has been intensively studied in several tumors, by inducing cell cycle arrest and apoptosis, inhibition of cell proliferation, and increasing cell sensitivity to DNA-damaging agents. Recently it was shown that FHIT controls the invasive phenotype of lung tumor cells by regulating the expression of genes associated with epithelial-mesenchymal transition such as vimentin or MMP-9 through an EGFR signaling pathway.

Human epidermal growth factor 2 (HER2/ERBB2/neu) is a member of the ERBB family of tyrosine kinase receptors, and is activated by homodimerization or heterodimerization with other ERBB receptors. Deregulation of HER2 gene, by overexpression and/or gene amplification has been proved important in breast and gastric cancer, in which overexpression of HER2 confers greater response to specific anti-HER2 treatment, including trastuzumab. In lung carcinogenesis, HER2 mutations are thought to be more clinically relevant than overexpression or gene amplification. HER2 mutations in NSCLC, described exclusively in adenocarcinoma histology, are present in approximately 4% of this subset of lung cancer patients.

SUMMARY OF THE INVENTION

The present invention relates to methods and pharmaceutical compositions for the treatment of lung cancer. In particular, the present invention is defined by the claims.

DETAILED DESCRIPTION OF THE INVENTION

The inventors showed that FHIT regulates HER2 activity in lung tumor cells and that HER2 inhibitors reduce invasion induced by FHIT inhibition.

Accordingly, one aspect of the present invention relates to a method of determining whether a patient suffering from a lung cancer is eligible to a treatment with a HER2 inhibitor comprising the steps of i) determining the expression level of FHIT in a tumor tissue sample obtained from the patient, ii) comparing the expression level determined at step i) with a predetermined reference value and iii) concluding that the patient is eligible to a treatment with a HER2 inhibitor when the expression level determined at step i) is lower than the predetermined reference level.

A further object of the present invention relates to a method of treating lung cancer in a patient in need thereof comprising the steps of i) determining the expression level of FHIT in a tumor tissue sample obtained from the patient, ii) comparing the expression level determined at step i) with a predetermined reference value and iii) administering to the patient a therapeutically effective amount of at least one HER2 inhibitor when the expression level determined at step i) is lower than the predetermined reference level.

A further object of the present invention relates to a method of determining whether a patient suffering from a lung cancer will achieve a response to a treatment with a HER2 inhibitor comprising the steps of i) determining the expression level of FHIT in a tumor tissue sample obtained from the patient, ii) comparing the expression level determined at step i) with a predetermined reference value and iii) concluding that the patient will achieve a response to a treatment with a HER2 inhibitor when the expression level determined at step i) is lower than the predetermined reference level.

As used herein, the term "lung cancer" includes, but is not limited to all types of lung cancers at all stages of progression like lung carcinomas metastatic lung cancer, non-small cell lung carcinomas such as lung adenocarcinoma or lung squamous carcinoma.

As used herein, the terms "HER2" and "ErbB2" have their general meaning ion the art and are used interchangeably herein and refer to human HER2 protein described, for example, in Semba et al., PNAS (USA) 82:6497-6501 (1985) and Yamamoto et al. Nature 319:230-234 (1986) (Genebank accession number X03363).

In some embodiments, the lung cancer is not associated with a HER2 mutation. HER2 mutations that are associated with lung cancer are well known in the art and typically include exon 20 insertions such as c. 2325_2326 ins12, p. A775_G776insYVMA; c. 2324_2325 ins12, p. A775_G776insYVMA; c. 2326_2327 ins3, p. G776>VC; c. 2339_2340 ins9, p. P780_Y781insGSP; c. 2322_2323 ins12, p. M774_A775insAYVM).

As used herein, the term "tumor tissue sample" has its general meaning in the art and encompasses pieces or slices of tissue that have been removed including following a surgical tumor resection. The tumor tissue sample can be subjected to a variety of well-known post-collection preparative and storage techniques (e.g., fixation, storage, freezing, etc.) prior to determining the cell densities. Typically, the tumor tissue sample is fixed in formalin and embedded in a rigid fixative, such as paraffin (wax) or epoxy, which is placed in a mould and later hardened to produce a block which is readily cut. Thin slices of material can be then prepared using a microtome, placed on a glass slide and submitted e.g. to immunohistochemistry (using an IHC automate such as BenchMark® XT, for obtaining stained slides).

As used herein, the term "FHIT" has its general meaning in the art and refers to fragile histidine triad gene (Gene ID: 2272). This gene, a member of the histidine triad gene family, encodes a diadenosine 5',5'''-P1,P3-triphosphate hydrolase involved in purine metabolism. Exemplary nucleic and amino acid sequences are typically referenced under NM_001166243.2 NP_001159715.1 (NCBI reference sequences).

Determining an expression level of a gene (e.g. FHIT) in a tumor sample obtained from a patient can be implemented by a panel of techniques well known in the art. Typically, an expression level of a gene is assessed by determining the quantity of mRNA produced by this gene.

Methods for determining a quantity of mRNA are well known in the art. For example, nucleic acid contained in the samples (e.g., cell or tissue prepared from the patient) is first extracted according to standard methods, for example using lytic enzymes or chemical solutions or extracted by nucleic-acid-binding resins following the manufacturer's instructions. Thus the extracted mRNA is then detected by hybridization (e.g., Northern blot analysis) and/or amplification (e.g., RT-PCR). Typically, quantitative or semi-quantitative RT-PCR is preferred. Real-time quantitative or semi-quantitative RT-PCR is particularly advantageous. Other methods of Amplification include ligase chain reaction (LCR), transcription-mediated amplification (TMA), strand displacement amplification (SDA) and nucleic acid sequence based amplification (NASBA), quantitative new generation sequencing of RNA (NGS).

Nucleic acids (polynucleotides) comprising at least 10 nucleotides and exhibiting sequence complementarity or homology to the mRNA of interest herein find utility as hybridization probes or amplification primers. It is understood that such nucleic acids need not be completely identical, but are typically at least about 80% identical to the homologous region of comparable size, more typically 85% identical and even more typically 90-95% identical. In some embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more typically of between 15 and 700, typically of between 20 and 500 nucleotides. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they typically hybridize under high stringency hybridization conditions (corresponding to the highest melting temperature Tm, e.g., 50% formamide, 5× or 6× SCC. SCC is a 0.15 M NaCl, 0.015 M Na-citrate). Nucleic acids which may be used as primers or probes in the above amplification and detection method may be assembled as a kit. Such a kit includes consensus primers and molecular probes. A preferred kit also includes the components necessary to determine if amplification has occurred. A kit may also include, for example, PCR buffers and enzymes; positive control sequences, reaction control primers; and instructions for amplifying and detecting the specific sequences.

In some embodiments, the methods of the invention comprise the steps of providing total RNAs extracted from cancer cells and subjecting the RNAs to amplification and hybridization to specific probes, more particularly by means of a quantitative or semi-quantitative RT-PCR.

Probes made using the disclosed methods can also be used for nucleic acid detection, such as in situ hybridization (ISH) procedures (for example, fluorescence in situ hybridization (FISH), chromogenic in situ hybridization (CISH) and silver in situ hybridization (SISH)) or comparative genomic hybridization (CGH). For instance, in situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques. Numerous procedures for FISH, CISH, and SISH are known in the art. For example, procedures for performing FISH are described in U.S. Pat. Nos. 5,447,841; 5,472,842; and 5,427,932; and for example, in Pinkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. J. Pathol. 157:1467-1472, 2000 and U.S. Pat. No. 6,942,970. Additional detection methods are provided in U.S. Pat. No. 6,280,929.

Probes are typically labelled with a detectable molecule. For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin.

Amplification of the FITC signal can be effected, if necessary, by incubation with biotin-conjugated goat antiavidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278. Numerous reagents and detection schemes can be employed in conjunction with FISH, CISH, and SISH procedures to improve sensitivity, resolution, or other desirable properties. As discussed above probes labeled with fluorophores (including fluorescent dyes and QUANTUM DOTS®) can be directly optically detected when performing FISH. Alternatively, the probe can be labeled with a nonfluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can be labeled with a fluorophore. In other examples, the probe is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publications Nos. 2006/0246524; 2006/0246523, and 2007/0117153.

It will be appreciated by those of skill in the art that by appropriately selecting labelled probe-specific binding agent pairs, multiplex detection schemes can be produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can be labelled with a first hapten, such as biotin, while a second probe that corresponds to a second target sequence can be labelled with a second hapten, such as DNP. Following exposure of the sample to the probes, the bound probes can be detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Probes typically comprise single-stranded nucleic acids of between 10 to 1000 nucleotides in length, for instance of between 10 and 800, more typically of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they typically hybridize under high stringency hybridization conditions (corresponding to the highest melting temperature Tm, e.g., 50% formamide, 5× or 6× SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In some embodiments, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

The expression level of a gene may be expressed as absolute expression level or normalized expression level. Both types of values may be used in the present method. The expression level of a gene is typically expressed as normalized expression level when quantitative PCR is used as method of assessment of the expression level because small differences at the beginning of an experiment could provide huge differences after a number of cycles.

Typically, expression levels are normalized by correcting the absolute expression level of a gene by comparing its expression to the expression of a gene that is not relevant for determining the cancer stage of the patient, e.g., a housekeeping gene that is constitutively expressed. Suitable genes for normalization include housekeeping genes such as the actin gene ACTB, ribosomal 18S gene . . . . This normalization allows comparing the expression level of one sample, e.g., a patient sample, with the expression level of another sample, or comparing samples from different sources.

Alternatively, the expression level of a gene (e.g. FHIT) may be determined at the protein level. For example, the tumor sample of the patient may be contacting with a binding partner specific for the protein of interest (i.e. FHIT).

In some embodiments, the binding partner is an antibody or an aptamer. Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies of the invention or a fragment thereof can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique. In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library.

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example, radioactive molecules include but are not limited radioactive atom for scintigraphic studies such as I123, I124, In111, Re186, Re188. Typically, the antibodies against the surface markers are already conjugated to a fluorophore (e.g. FITC-conjugated and/or PE-conjugated).

In some embodiments, immunostained slices of the tumor tissue sample may be obtained with an automated slide-staining system by using a labelled binding partner as above described (e.g. an antibody). Immunochemistry (IHC) is a suitable method for quantifying the expression level of a marker in a tissue sample. Typically, the tumor sample is typically fixed in formalin and embedded in a rigid fixative, such as paraffin (wax) or epoxy, which is placed in a mould and later hardened to produce a block which is readily cut. Thin slices of material are prepared using a microtome, placed on a glass slide and submitted to immunohistochemistry, for example using an IHC automate such as Bench-Mark® XT allowing automatic stained slide preparation for implementing the immunohistochemical staining. Then after digitalisation of the slices may be used to quantify the level of the marker. Digitalisation of the slices may be made by scan capture, for example with a high resolution Hamamatsu NanoZoomer® 2.0-HT scanner. The mean, median, min and max of the relevant staining intensity of all positive stained cells detected in the tumour sample may be provided. The values and the distribution of the staining intensity can be compared to the predetermined reference value.

Typically, the predetermined reference value is a threshold value or a cut-off value. A "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of the expression level of FHIT in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of FHIT in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator the reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the methods of the present invention further comprises a) determining the expression level of pHER2, b) comparing the level determined at step a) with its corresponding predetermined reference value. More particularly, a further object of the present invention relates to a method of determining whether a patient suffering from a lung cancer is eligible to a treatment with a HER2 inhibitor comprising the steps of i) determining the expression level of FHIT and pHER2, ii) comparing the levels determined at step i) with their corresponding predetermined reference values and iii) concluding that the patient is eligible to a treatment with a HER2 inhibitor when the expression level determined for FHIT is lower than is corresponding predetermined reference level and the level of pHER2 is higher than its corresponding predetermined reference value.

As used herein, the term "pHER2" has its general meaning in the art and relates to the phosphorylated form of HER2. Phosphorylation of HER2 is a indeed precondition for downstream signalling and represents the functional and active form of HER2. The main site of auto-phosphorylation of HER2 is on tyrosine 1248 residue (Tyr1248) (Cicenas J, Urban P, Ming W, Vuaroqueaux V, Labuhn M, Wight E, Eppenberger U, Eppenberger-Castori S: Phosphorylation of tyrosine 1248-ERBB2 measured by chemiluminescence-linked immunoassay is an independent predictor of poor prognosis in primary breast cancer patients. Eur J Cancer 42: 636-645).

Methods for determining the level of pHER2 are well known in the art and typically involved the use of antibody directed said phosphorylated form. For example, primary mouse monoclonal antibodies against phosphorylated HER2 on Tyr1248 are commercially available (e.g. HER2-pY-1248, clone PN2A; Dako).

As used herein the term "HER2 inhibitor" refers to an agent which interferes with HER2 activation or function. Examples of HER2 inhibitors include HER2 antibodies; small organic molecule HER2 antagonists; HER2 tyrosine kinase inhibitors; antisense molecules; and/or agents that bind to, or interfere with function of, downstream signaling molecules, such as MAPK or Akt. Typically, the HER2 inhibitor is an antibody or a small organic molecule. Methods to determine HER2-inhibitors are known in the art, for example as described in detail in EP1877398.

In some embodiments, the HER2 inhibitor is an "anti-HER2 antibody" which is an antibody that binds to a HER2 receptor, in particular the extracellular domain of HER2.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). In some embodiments, the anti-HER antibody is a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). In some embodiments, the anti-HER antibody is a humanized antibody. "Humanized" forms of non-human (e.g., murine) antibodies are chimeric antibodies that contain minimal sequence derived from non-human immunoglobulin. In some embodiments, the anti-HER antibody is a human antibody. A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. In some embodiments, the anti-HER antibody is a single domain antibody. The term "single domain antibody" (sdAb) or "VHH" refers to the single heavy chain variable domain of antibodies of the type that can be found in Camelid mammals which are naturally devoid of light chains. Such VHH are also called "nanobody®". According to the invention, sdAb can particularly be llama sdAb.

In some embodiments, the HER2 inhibitor is a small organic molecule. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000da, and most preferably up to about 1000 Da.

Examples of HER2 inhibitors include pertuzumab, trastuzumab, dacomitinib, (HER2) antibodies as described in WO-2012162561, neratinib, aliitinib tosylate, poziotinib, CUDC-101 (Curis), BT-211 1 (biOsasis), margetuximab, Exelixis, NT-004 or NT-113 (Jiangsu Kanion Pharmaceutical Co Ltd), S-22261 1 (Shionogi & Co Ltd), AG879, Mubritinib, AC-480 (Bristol-Myers Squibb Co), sapitinib, MM-111 (Merrimack Pharmaceuticals inc), PR-810 (University of Auckland), cipatinib trastuzumab-duocarmycin, Prolanta, varlitinib, kahalalide F, TrasGEX, masoprocoi, ARRY-380 (Cascadian Therapeutics), erbicinumab, Hu ax-Her2, CP-724714 (Pfizer), COVA-208 (Covagen), iapatinib and pazopanib, AEE-788 (Novartis), canertinib, pilitinib, BMS-690514 (Brisiol-Meyers Squibb), afatinib, dacomitinib, derivates and salts thereof. In some embodiments, the HER2 inhibitor is N4-(4-([1,2,4]Triazolo[1,5-a]pyridin-7-yloxy)-3-methylphenyl)-N6-(4,4-dimethyl-4,5-dihydrooxazol-2-yl)quinazoline-4,6-diamine (also called "ARRY-380"), which has the structure:

is a selective ErbB2 (HER2) inhibitor described in WO 2007/059257, which is incorporated by reference in its entirety.

In some embodiments, the HER2 inhibitor is an inhibitor of expression. An "inhibitor of expression" refers to a natural or synthetic compound that has a biological effect to inhibit the expression of a gene. Therefore, an "inhibitor of HER2 expression" denotes a natural or synthetic compound that has a biological effect to inhibit the expression of HER2 receptor. Typically, the inhibitor of gene expression is a siRNA, an antisense oligonucleotide or a ribozyme. Inhibitors of gene expression for use in the present invention may be based on antisense oligonucleotide constructs. Anti-sense oligonucleotides, including anti-sense RNA molecules and anti-sense DNA molecules, would act to directly block the translation of the HER2 receptor mRNA by binding thereto and thus preventing protein translation or increasing mRNA degradation, thus decreasing the level of the HER2 receptor, and thus activity, in a cell. For example, antisense oligonucleotides of at least about 15 bases and complementary to unique regions of the mRNA transcript sequence encoding the HER2 receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the HER receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays. Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

As used the term "therapeutically effective amount" refers to an amount of a drug (e.g. HER2 inhibitor) effective to treat lung cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete respose, CR), improve survival (including overall survival and progression free survival) and/or improve one or more symptoms of cancer (e.g. as assessed by FOSI). Most preferably, the therapeutically effective amount of the drug is effective to improve progression free survival (PFS) and/or overall survival (OS). By "extending survival" is meant increasing overall or progression free survival in a treated patient relative to an untreated patient (i.e. relative to a patient not treated with a HER2 inhibitor), or relative to a patient who does not express a HER2 receptor at the designated level. Typically, the therapeutically effective amount is the amount which leads to an objective response, a partial response or a complete response. An "objective response" refers to a measurable response, including complete response (CR) or partial response (PR). By "complete response" or "CR" is intended the disappearance of all signs of cancer in response to treatment. This does not always mean the cancer has been cured. "Partial response" or "PR" refers to a decrease in the size of one or more tumors or lesions, or in the extent of cancer in the body, in response to treatment. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The compounds of the invention (i.e. HER2 inhibitors) are administered as a formulation in association with one or more pharmaceutically acceptable excipients to form pharmaceutical composition. As used herein, the term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Pharmaceutical compositions suitable for the delivery of compounds of the present invention and methods for their preparation will be readily apparent to those skilled in the art. In the pharmaceutical compositions of the present invention for oral, sublingual, subcutaneous, intramuscular, intravenous, transdermal, local or rectal administration, the active principle (i.e. a compound of the invention), alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. In particular, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Compounds of the invention can be formulated into a composition in a neutral or salt form as above described. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the compounds of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Compounds of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1: FHIT loss is correlated to HER2 activation in vivo in human NSCLC. A. Western blot analysis showing a negative correlation between FHIT level and HER2 activation rate (pHER2/tHER2) in a series of 48 cases of NSCLC; B. Immunohistochemistry analysis showing mirror-images of FHIT and pHER2 labellings on serial sections of two NSCLC cases. Abbreviations: pHER2, phospho-HER2; tHER2, total HER2.

FIG. 4: Collagen I gel invasion by A549 spheroids induced by FHIT silencing is HER2-dependent. Timelapse videomicroscopy of tumor cell dispersion from the spheroids into the collagen I matrix showing that irbinitinib (15 nM) reduces spheroid invasion induced by FHIT silencing in A549 cell line (scrambled+DMSO vs. FHIT siRNA+DMSO: p=0.0036; FHIT siRNA+DMSO vs. FHIT siRNA+irbinitinib: p=0.0001). A. Representative phase-contrast images of spheroids at T0 and T=72h. B. Time course analysis of mean diameter of spheroids. p<0.01; * p<0.001.

EXAMPLE

The lack or decrease of FHIT (fragile histidine triad) expression is a common event in lung cancer. We recently showed that FHIT acts as a suppressor of tumor invasion.

Indeed, FHIT controls the invasive phenotype of lung tumor cells by regulating the expression of genes associated with epithelial-mesenchymal transition such as vimentin or MMP-9 through an EGFR signaling pathway. Accordingly, we focused on another member of this receptor tyrosine kinase family: HER2.

Figure 1A:
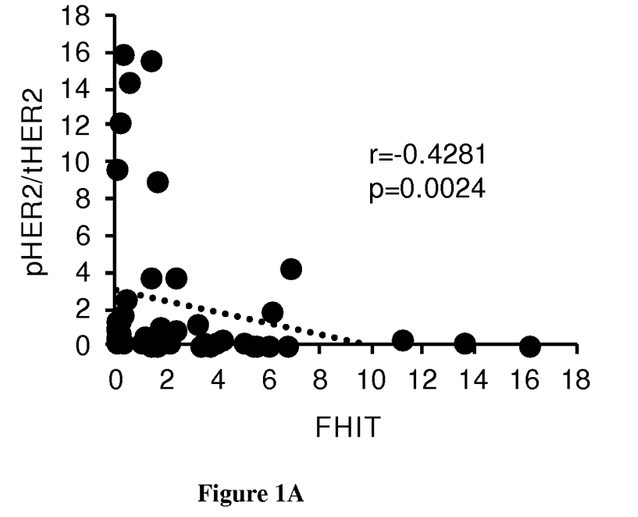
Figure 1B:
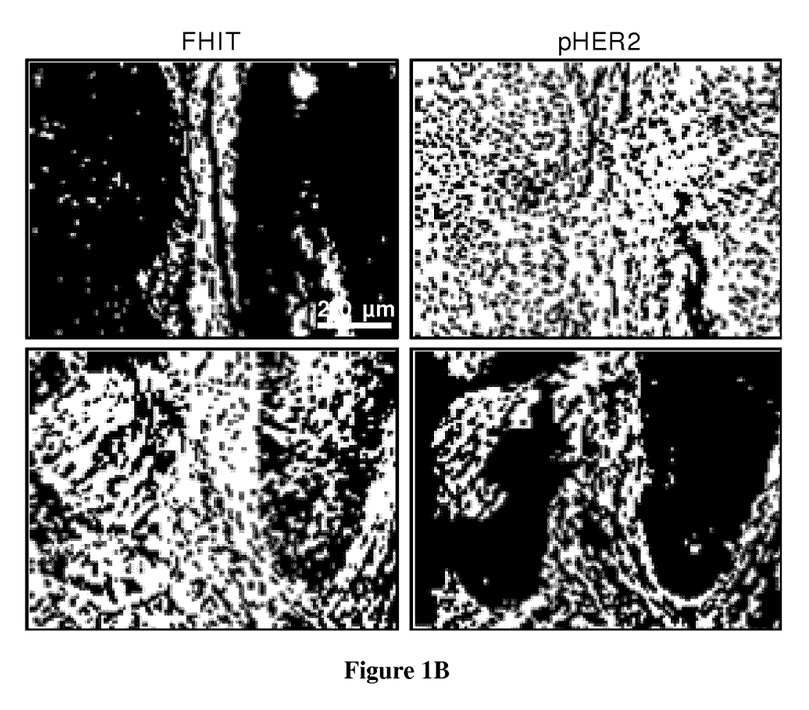
Figure 2:
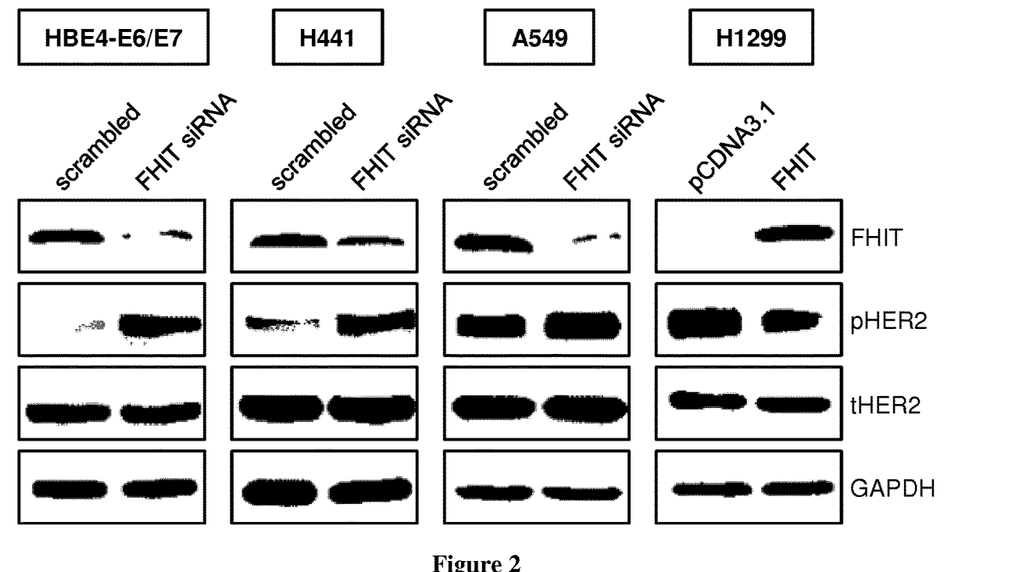
FIG. 2: Modulation of FHIT expression regulates HER2 activation. Western blot analysis of FHIT, pHER2 and tHER2 after FHIT silencing in HBE-4-E6/E7, H441 and A549 cell lines transiently transfected by FHIT siRNA or the scrambled control and after FHIT overexpression in H1299 cell line stably transfected by FHIT cDNA or the control empty vector. GAPDH serves as loading control.

First, we observed in vivo, by immunohistochemistry and western blotting in a series of non-small cell lung cancer samples, a negative correlation between FHIT expression and the activated form of HER2 (pospho-HER2, pHER2) (FIG. 1). This correlation was also observed in vitro in a panel of lung cell lines; the most invasive cell lines expressing low level of FHIT and high level of pHER2. Moreover, the inhibition through siRNA or overexpression by stable transfection with cDNA of FHIT led to respectively an increase or decrease of HER2 receptor activity (FIG. 2).

Figure 3A:
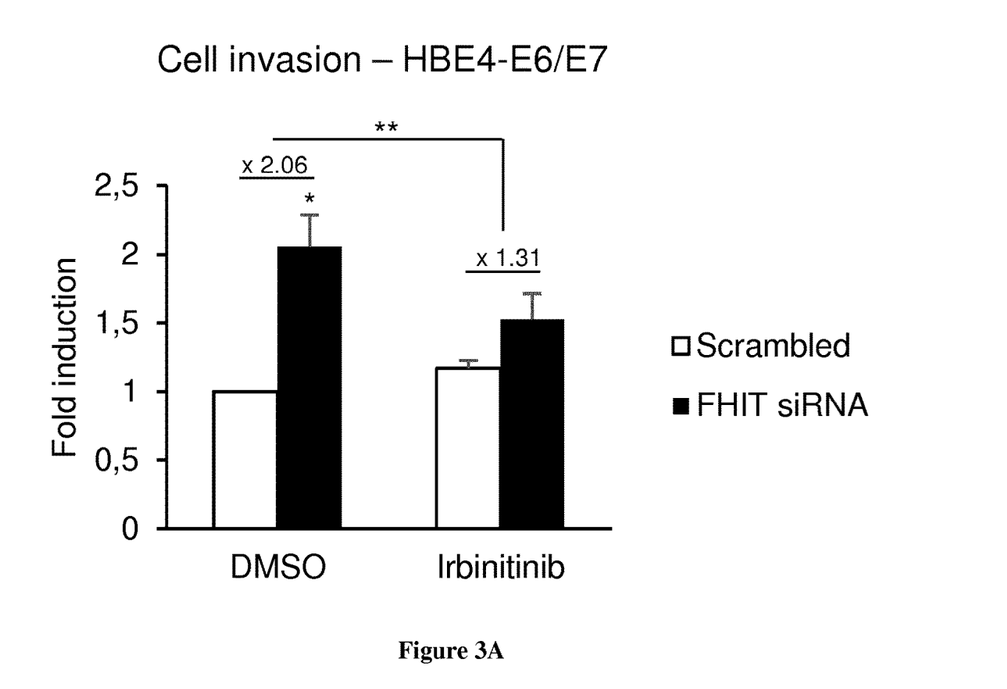
FIG. 3: Cell invasion induced by FHIT silencing is HER2-dependent. Analysis of cell invasion capacities in a matrigel modified Boyden chamber assay showing that HER2 inhibitor, irbinitinib, (10 nM) reduces cell invasion induced by FHIT silencing in HBE-4-E6/E7 (A) and A549 (B) cell lines, respectively. * p<0.05; ** p<0.01.
Figure 3B:
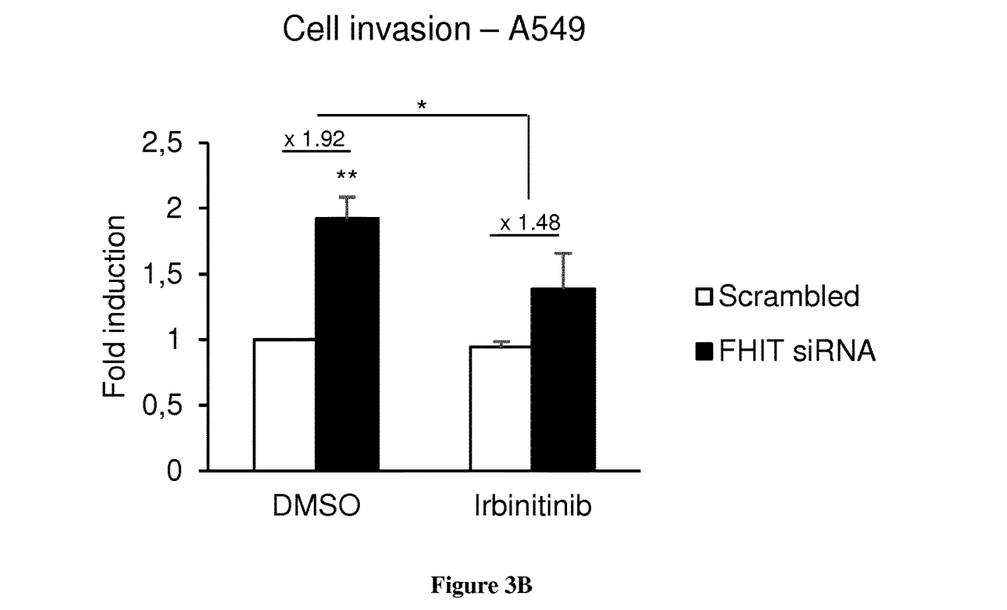
Figure 4A:
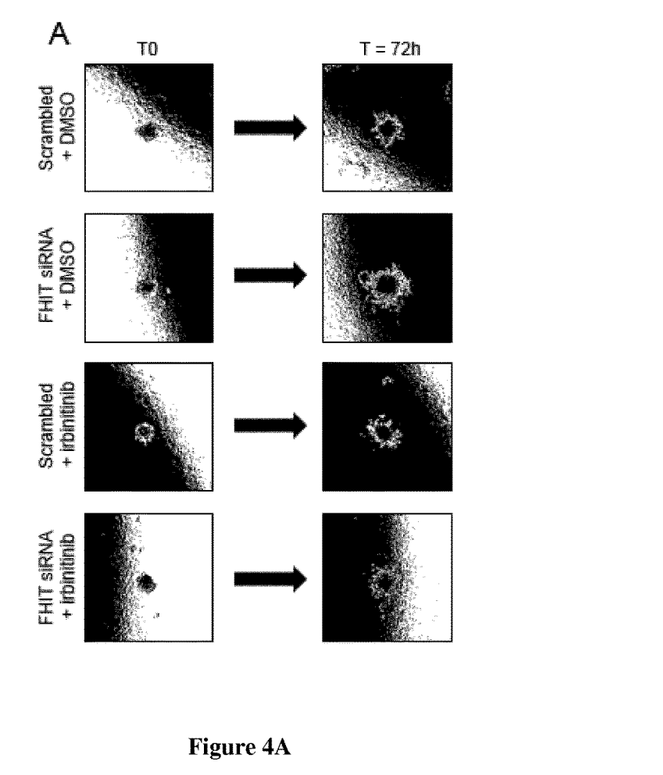
Figure 4B:
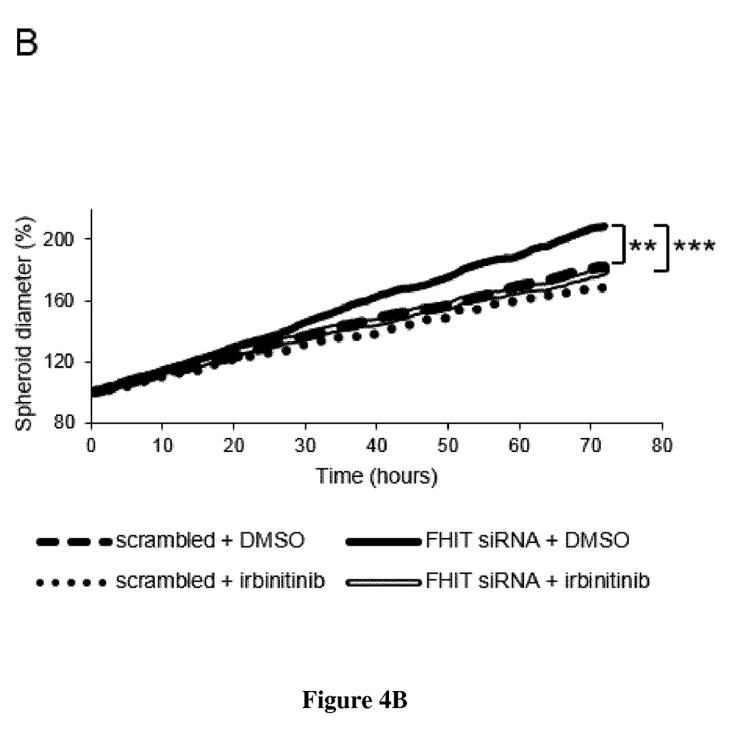

The use of a specific inhibitor, Irbinitinib (ARRY-380; ONT-380), allowed to demonstrate that the invasion induced by FHIT inhibition is HER2-dependent in two complementary models: a modified Boyden chamber assay mimicking basement membrane crossing (FIG. 3) and a 3D model of cell spheroids embedded in collagen matrix mimicking stroma infiltration by tumor cells (FIG. 4).

In conclusion, we showed that FHIT regulates HER2 activity in lung tumor cells and that a HER2 inhibitor reduces invasion induced by FHIT inhibition. This study would allow for the identification of new therapeutic leads for lung cancer.

REFERENCES

Throughout this application, various references describe the state of the art to which this invention pertains. The disclosures of these references are hereby incorporated by reference into the present disclosure.

The invention claimed is:

1. A method of treating lung cancer in a patient in need thereof comprising the steps of i) determining the expression level of FHIT in a tumor tissue sample obtained from the patient, ii) comparing the expression level determined at step i) with a predetermined reference value, iii) determining that the expression level of FHIT is lower than the predetermined reference level, and iv) administering to the patient a therapeutically effective amount of at least one HER2 inhibitor, wherein the at least one HER2 inhibitor is selected from HER2 antibodies; small organic molecule HER2 antagonists; and/or HER2 tyrosine kinase inhibitors.

2. The method of claim 1 wherein the HER2 inhibitor is an anti-HER2 antibody which is an antibody that binds to a HER2 receptor, wherein the antibody that binds to a HER2 receptor binds to the extracellular domain of HER2.

3. The method of claim 1 wherein the HER2 inhibitor is a small organic molecule.

4. The method of claim 1 wherein the HER2 inhibitor is selected from the group consisting of pertuzumab, trastuzumab, dacomitinib, neratinib, allitinib tosylate, poziotinib, CUDC-101, BT-2111, margetuximab, NT-004, NT-113, S-222611, AG879, Mubritinib, AC-480, sapitinib, MM-111, cipatinib, trastuzumab-duocarmycin, human prolactin with a G129R mutation, varlitinib, kahalalide F, masoprocol, ARRY-380, erbicinumab, a human monoclonal antibody which binds HER2, CP-724714, COVA-208, lapatinib, pazopanib, AEE-788, canertinib, pelitinib, BMS-690514, afatinib, dacometinib, and salts thereof.

5. The method of claim 1, wherein the lung cancer is not associated with a HER2 mutation.

6. A method of treating lung cancer in a patient in need thereof comprising the steps of i) determining the expression level of FHIT and pHER2 in a tumor tissue sample obtained from the patient, ii) comparing the expression level of FHIT and pHER2 determined at step i) with its corresponding predetermined reference value, iii) determining that the expression level of FHIT is lower than the predetermined reference level and that the expression level of pHER2 is higher than the predetermined reference level, and iv) administering to the patient a therapeutically effective amount of at least one HER2 inhibitor, wherein the at least one HER2 inhibitor is selected from HER2 antibodies; small organic molecule HER2 antagonists; and/or HER2 tyrosine kinase inhibitors.

* * * * *